United States Patent
Adelberg et al.

(10) Patent No.: US 11,140,840 B2
(45) Date of Patent: Oct. 12, 2021

(54) PLANT PROPAGATION SYSTEM AND METHOD

(71) Applicants: Pioneer Hi-Bred International, Inc., Johnston, IA (US); Clemson University, Clemson, SC (US)

(72) Inventors: Jeffrey Adelberg, Clemson, SC (US); Amber E. Heck, Madison, WI (US); David Dallinger Kurth, Grimes, IA (US); Justine M. Olszewski, Johnston, IA (US)

(73) Assignees: Pioneer Hi-Bred International, Inc., Johnston, IA (US); Clemson University Research Foundation, Clemson, SC (US)

( * ) Notice: Subject to any disclaimer, the term of this patent is extended or adjusted under 35 U.S.C. 154(b) by 635 days.

(21) Appl. No.: 15/578,412

(22) PCT Filed: Jun. 2, 2016

(86) PCT No.: PCT/US2016/035389
§ 371 (c)(1),
(2) Date: Nov. 30, 2017

(87) PCT Pub. No.: WO2016/196714
PCT Pub. Date: Dec. 8, 2016

(65) Prior Publication Data
US 2018/0206427 A1    Jul. 26, 2018

Related U.S. Application Data

(60) Provisional application No. 62/169,912, filed on Jun. 2, 2015.

(51) Int. Cl.
*A01G 9/10* (2006.01)
*A01H 4/00* (2006.01)

(52) U.S. Cl.
CPC .............. *A01H 4/001* (2013.01); *A01H 4/00* (2013.01); *A01H 4/005* (2013.01)

(58) Field of Classification Search
CPC .......... A01H 4/00; A01H 4/001; A01H 4/003; A01H 4/005; A01G 9/02; A01G 9/027;
(Continued)

(56) References Cited

U.S. PATENT DOCUMENTS 3,515,036 A * 6/1970 Akira ................. B31D 3/02
493/334
3,739,522 A * 6/1973 Greenbaum ......... A01G 9/0295
47/87
(Continued)

FOREIGN PATENT DOCUMENTS

CN    104387540 A * 3/2015 ............... C08G 8/00
EP      0254434 A2 * 1/1988 ........... A01G 9/0295
WO   WO 2014/197442    12/2014

OTHER PUBLICATIONS

Repotting seedlings 101 by Niki Jabbour (https://savvygardening.com/repotting-seedlings-101/) Wayback Machine Internet Archived on Apr. 24, 2015 (Year: 2015).*
(Continued)

*Primary Examiner* — Peter M Poon
*Assistant Examiner* — Danielle A Clerkley
(74) *Attorney, Agent, or Firm* — Dority & Manning, P.A.

(57) ABSTRACT

A plant propagation system is described that can be utilized for micropropagation through early stages of plant development. A system can include multiple plant support matrices, containers for the matrices, and optionally a tool for separating sections of a plant support matrix from the remainder of the matrix. During use developing plant tissue can be transferred between matrices and growth media can be varied with little or no damage to developing plant tissue and
(Continued)

lower chances for contamination of the developing plant tissues.

7 Claims, 10 Drawing Sheets

(58) Field of Classification Search
CPC ...... A01G 9/028; A01G 9/029; A01G 9/0293; A01G 9/0295; A01G 24/44
USPC .................. 47/65, 66.1, 66.5, 73, 77
See application file for complete search history.

(56) References Cited

U.S. PATENT DOCUMENTS

| | | | | |
|---|---|---|---|---|
| 3,883,989 | A * | 5/1975 | Melvold | A01G 24/60 47/73 |
| 3,961,445 | A * | 6/1976 | Rack | A01G 9/0291 47/74 |
| 3,973,355 | A * | 8/1976 | McKenzie | A01G 24/44 47/59 R |
| 4,034,508 | A * | 7/1977 | Dedolph | A01H 4/001 47/84 |
| 4,132,337 | A * | 1/1979 | Masuda | A01C 11/02 225/5 |
| 4,278,035 | A | 7/1981 | Pickett et al. | |
| 5,119,588 | A * | 6/1992 | Timmis | C12N 5/04 435/297.5 |
| 5,438,796 | A * | 8/1995 | Nathan | A01G 9/0295 47/66.6 |
| 5,525,505 | A | 6/1996 | Young et al. | |
| 5,548,924 | A | 8/1996 | Mekler | |
| 5,597,731 | A | 1/1997 | Young et al. | |
| 5,804,261 | A * | 9/1998 | Schwarzenberg | A01G 5/04 248/27.8 |
| 6,185,864 | B1 | 2/2001 | Lee | |
| 6,381,901 | B1 * | 5/2002 | Friedman | A01G 9/028 206/752 |
| 6,526,693 | B2 * | 3/2003 | Cochran | A01G 9/028 47/33 |
| 6,753,178 | B2 | 6/2004 | Adelberg et al. | |
| 8,474,181 | B2 * | 7/2013 | Whitehead | B65D 3/20 47/66.4 |
| 10,470,378 | B2 * | 11/2019 | Shaffer | A01G 9/0291 |
| 2005/0155101 | A1 | 7/2005 | Akai et al. | |
| 2007/0196915 | A1 | 8/2007 | Tagawa et al. | |
| 2011/0232189 | A1 | 9/2011 | Bijl | |
| 2014/0259910 | A1 * | 9/2014 | Dunn | A01G 9/02 47/65.5 |
| 2014/0338259 | A1 | 11/2014 | Nilsson et al. | |
| 2014/0373445 | A1 * | 12/2014 | Bangera | A01H 4/001 47/1.01 R |
| 2016/0174469 | A1 * | 6/2016 | Shaffer | A01G 9/0291 47/66.7 |
| 2018/0002659 | A1 | 1/2018 | Hagihara et al. | |

OTHER PUBLICATIONS

International Search Report, dated Aug. 19, 2016, 8 pages.
International Preliminary Report on Patentability, dated Dec. 14, 2017. 8 pages.

* cited by examiner

PLANT PROPAGATION SYSTEM AND METHOD

CROSS REFERENCE TO RELATED APPLICATION

This application claims filing benefit of U.S. Provisional Patent Application No. 62/169,912, having a filing date of Jun. 2, 2015, which is incorporated herein by reference in its entirety.

BACKGROUND

Tissue culture propagation (also known as micropropagation) is the process of growing new plants from tissue that has been extracted from a parent plant. Tissue culture propagation is typically used for commercial plant propagation and genetic transformation. Known methods can provide a relatively high production efficiency, cleanliness and greater uniformity of plants. For example, in genetic transformation applications, foreign DNA is introduced into a plant's genome by plasm ids during co-culture with tissue, for instance via an *Agrobacterium* vector or particle bombardment. After initial selection for successfully transformed tissue, the tissue is cultured to regenerate monopolar shoots and root or to form bipolar embryos and then cultivated to develop to sexual maturity for, e.g., use in breeding programs. A similar process but for the genetic transformation step is carried out for plant propagation.

Micropropagation is generally described according to separate phases, each of which includes growth stages. Phase I generally includes those stages in which the plant tissue is primarily heterotrophic and comprised of undifferentiated or dedifferentiated cells. Stage I comprises initiation, in which explanted donor tissue is initiated in a growing media and, in the case of a transformation process, the tissues are co-cultured with the vector containing the foreign DNA. Stage II comprises a multiplication phase in which nutrients and hormones are provided to enable rapid cell division and substantial growth of callus or meristematic stem cells. Regeneration and propagation of Stage II transformation tissues results in cells that contain the successfully introduced foreign DNA.

In the early stages, it is very important to keep pathogens and biological pests from infesting the culture. Accordingly, the culture is generally held in an environment that shields the maturing plantlet from pathogens while also facilitating rapid and vigorous growth. In the first two stages of growth there are high metabolic requirements for energy consumption, but the plant tissue is not generally capable of carrying out adequate photosynthesis to meet this high demand for energy. Thus, these stages are accomplished heterotrophically. During Phase I, the plant tissue is typically exposed to adequate light intensity to signal chlorophyll development and organic carbon is obtained from sugar such as sucrose that is provided in a growth media.

In the second phase of development, cell differentiation takes place, leaves and shoots expand, and the plantlet becomes more photoautotrophic. During Stage III, the plant tissue becomes able to derive energy when exposed to light, gases, water and essential nutrients through the process of photosynthesis. In Stage IV, the plant is further matured, and the plant may begin to take on larger amounts of light and heat, developing roots and becoming strong enough for transfer to a greenhouse or the external environment.

The delicate state of the developing plant tissue has led to difficulties in successfully carrying out micropropagation on a large scale. For instance, the nutrients required during the early heterotrophic stages of growth are easily targeted by microorganisms that can destroy the young plantlets. Moreover, transplanting the plantlets from one growth media to another and/or from one growth environment to another will often damage the developing plant tissue, leading to slower growth and development or even plant destruction.

One particularly difficult transition is when the early stage culture begins to become photoautotrophic and develop leaves and shoots. The liquid growth media for the later stages is different than that for the earlier stages, and as the callus develops, overgrowth can lead to a lack of isolation when containment is breached, which can lead to a loss of integrity and/or contamination between individual plantlets. This transition can damage the young plantlets and introduce contamination due to handling.

Another difficult transition is when rooted plantlets are stronger and the plant has become photoautotrophic. The liquid growth media must be changed, with any sugar-containing materials removed and the rooted plantlet moved to a different growth media (e.g., soil). The soft roots are easily broken and often the roots are simply cut off and the resulting plantlets (micro-cuttings) forced to re-root in soil under mist in a shaded greenhouse. This is damaging to the plantlet, but economic forces require the use of micro-cuttings to be a preferred practice.

What is needed in the plant propagation industry is a method and system for producing plants in a manner that addresses such problems. For instance, a system that provides for growth media variation and young plantlet isolation is desired. Furthermore, a system and method of safely transplanting plantlets with little or no damage to the developing structures and little or no opportunity for contamination would be of great benefit. Additionally, what are needed are systems that can better integrate the laboratory with the greenhouse nursery.

SUMMARY

According to one embodiment, disclosed is a system for plant propagation. The system can include a plant tissue cassette and a receiver. The plant tissue cassette includes a plurality of support areas. Each support area is separable from the remainder of the cassette and each support area is capable of supporting plant material held in conjunction with a liquid growth media. The receiver includes a plurality of receiving areas. Each receiving area is separable from the remainder of the receiver. Each of the receiving areas is of a size to support a support area of the plant tissue cassette.

The system can also include a first container for the plant tissue cassette and a second container for the receiver. Each container can enclose at least a portion of the cassette and the receiver, respectively, and can be liquid impermeable so as to contain an amount of a liquid growth media. In one embodiment, one or both of the containers can be semi-permeable and can be of a size so as to completely enclose the plant tissue cassette or the receiver. In addition, one or both of the containers can be sealable so as to isolate the plant tissue cassette or the receiver inside of the container.

Also disclosed herein is a method for plant propagation. For instance, a method can include locating plant material on a support area of a plant tissue cassette and cultivating the plant material in a first liquid growth media for a period of time while the plant material is supported on the plant tissue cassette. Following this period of cultivation, the method can include separating the support area from the remainder of the plant tissue cassette and locating the support area and the plant material thereon on a receiving area of a receiver. The method also includes further cultivating the plant material in a second liquid growth media while the plant material is supported on the receiving area.

In one embodiment, the support area holding the plant material can be separated from the remainder of the plant tissue cassette by use of a tool, which can prevent contamination of and damage to the developing plant material during the movement of the plant material from one support vessel to another and from one growth media to another.

BRIEF DESCRIPTION OF THE DRAWINGS

A full and enabling disclosure, including the best mode thereof, to one of ordinary skill in the art, is set forth more particularly in the remainder of the specification, including reference to the accompanying Figures, in which.

DETAILED DESCRIPTION

Figure 1:
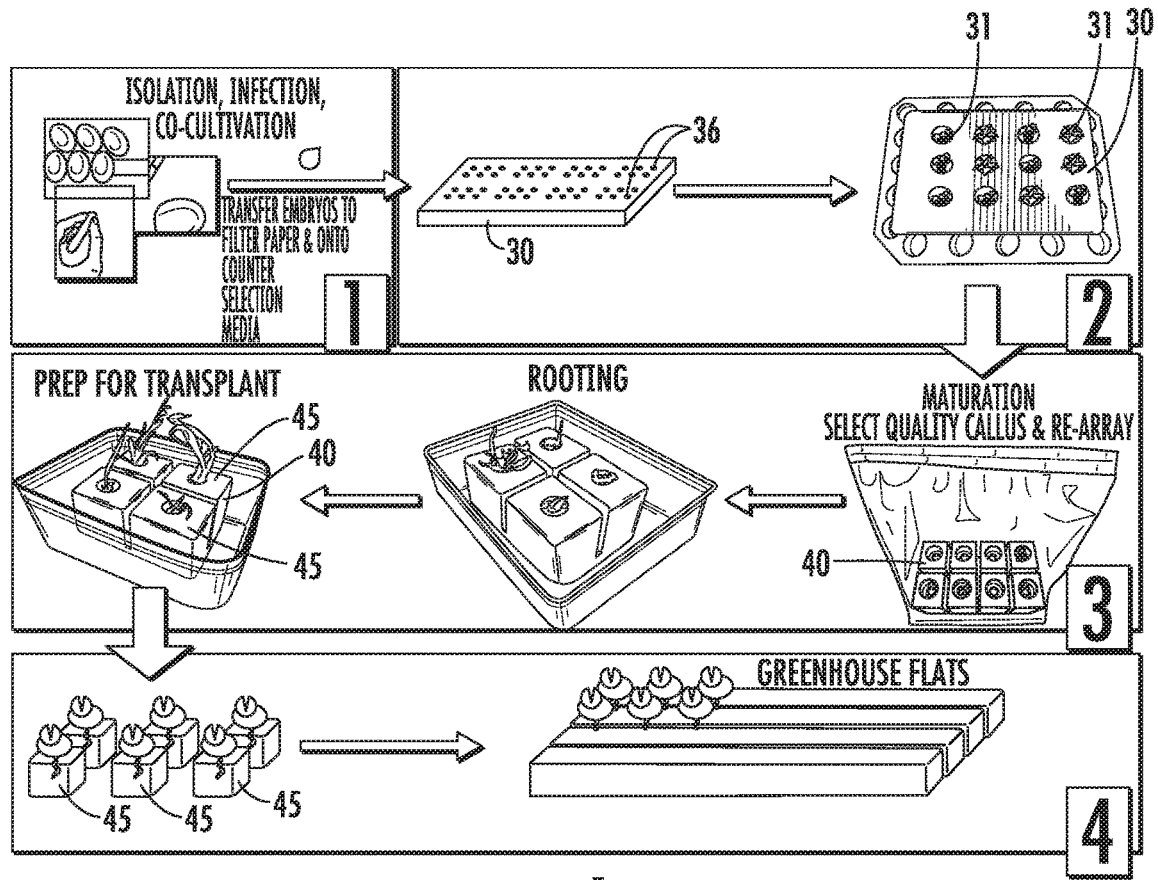
FIG. 1 illustrates one embodiment of a system and method as disclosed herein including a first stage 1 of explant preparation, a second stage 2 of cell cultivation, a third stage 3 of regeneration and growth, and a fourth stage 4 of acclimatization.

Reference will now be made in detail to various embodiments of the presently disclosed subject matter, one or more examples of which are set forth below. Each embodiment is provided by way of explanation, not limitation, of the subject matter. In fact, it will be apparent to those skilled in the art that various modifications and variations may be made to the present disclosure without departing from the scope or spirit of the disclosure. For instance, features illustrated or described as part of one embodiment, may be used in another embodiment to yield a still further embodiment. Thus, it is intended that the present disclosure cover such modifications and variations as come within the scope of the appended claims and their equivalents.

As used herein, the term "autotrophic" with regard to plant material generally refers to plant tissue that is capable of photosynthesis. As a result, external energy-supplying compounds are not required in order for autotrophic plant material to sustain a normal growth rate.

As utilized herein, the term "bud" generally refers to an organized mass of differentiated plant tissues from which a shoot or flower will develop.

As utilized herein, the term "callus" generally refers to dedifferentiated totipotent embryogenic plant cells that temporarily gain the ability to proliferate and/or regenerate an embryo and which, at least at a macroscopic level, are either unconnected or loosely connected. Callus generally arises from culturing of an explant.

As utilized herein, the term "embling" generally refers to a plantlet grown from a somatic embryo that is sufficiently developed for transplantation into soil.

As utilized herein, the term "explant" generally refers to a piece of plant tissue excised from a donor plant for culturing in vitro as the source of cultured plant tissues.

As used herein, the term "heterotrophic" generally refers to plant tissue, including cultured somatic embryos, that is incapable or at most weakly capable of photosynthesis. Heterotrophic plant material requires an extraneous source of carbon such as sucrose that is provided in a growth medium to provide energy and maintain normal growth and development at a desired rate.

As utilized herein, the term "meristematic cells" generally refers to undifferentiated totipotent plant stem cells that are capable of differentiation as well as those capable of regeneration to form new stem cells. Meristematic cells include cells from any of the root apical meristem, the shoot apical meristem, or the vascular meristem of a plant.

As utilized herein, the term "plantlet" generally refers to a small plant with a shoot and root pole, but more immature than a seedling. A plantlet is usually heterotrophic, but may also be autotrophic.

As utilized herein, the term "seedling" generally refers to a plant developed from a germinating seed to autotrophic growth.

As utilized herein, the term "somatic embryo" generally refers to a plant embryonic structure arising from an explanted somatic tissue (e.g., via callus), zygotic embryo or other totipotent plant tissue (e.g., meristematic tissue).

As utilized herein, the term "zygotic embryo" generally refers to a plant embryo that has developed directly from the zygote produced from the sexual fusion of gametes. For example, the embryo found in a seed is a zygotic embryo.

The present disclosure is generally directed to a plant propagation system that can be utilized for micropropagation through early stages of plant development. More specifically, disclosed systems can provide for plant tissue transfer and growth media change with little or no damage to developing plant tissue and lower chances for contamination of the developing plant tissues. Disclosed systems can provide labor and other cost savings as well as increased rates of successful adult plant generation through elimination of hands-on manual tissue transfers and improved growth media alteration throughout the early stages of plant development.

More specifically, the plant propagation system can include at least two tissue support matrices and vessel systems that can contain and at least partially enclose a tissue support matrix that can be held in the vessel in conjunction with a liquid growth media. A tissue support matrix can provide benefits to a system including one or more of support of plant material during early stages of micropropagation, allowance of aseptic media infusion and removal, creation of mechanical opportunities to handle a plurality of embryonic tissue events, and the maintaining of identity of unique events throughout a development process. Vessel systems can be economical, can have few components, can be robust in the environment in which the systems can be utilized and transported, can allow tissue inspection, can lessen disposable waste materials, and/or can facilitate mechanized handling at transfer of developing plant material between environments.

FIG. 1 illustrates one embodiment of a system and micropropagation process. A method as illustrated in FIG. 1 can include four stages. The basic stages of the micropropagation process can include a first stage 1 that includes explant preparation and, in certain embodiments, transformation; a second stage 2 during which explanted dedifferentiated or undifferentiated cells are cultivated to multiply; a third stage 3 that can include regeneration and growth of a differentiated organism; and a fourth stage 4 that can include acclimatization to a greenhouse or natural environment.

In the initial stage 1, explant material can be selected for propagation. In the particular embodiment of a transformation event, the explant material can be infected and/or co-cultivated with a vector carrying the heterogenic genetic information. Following initial co-cultivation according to standard practice, the embryonic tissue can be selected for successful transformation and located (e.g., via pipetting or via any other suitable fashion) on a tissue support matrix for stage 2 growth. The tissue support matrix utilized during this early stage development is referred to herein as a plant tissue cassette 30.

In general, a tissue support matrix can be formed of a self-supporting rigid or semi-rigid cohesive material having fixed dimensions that can support developing plant tissue, can withstand sterilization procedures, and in one embodiment can provide form and stability to a flexible container that can be utilized in conjunction with the support matrix.

Figure 2:
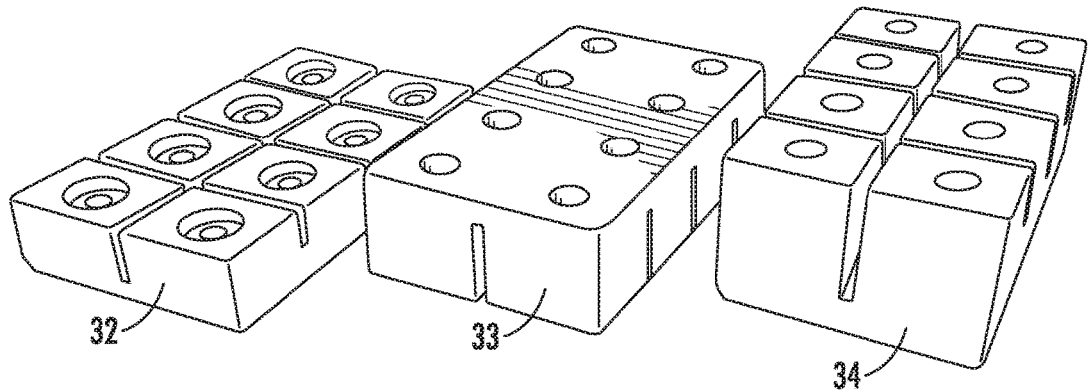
FIG. 2 illustrates three embodiments of tissue support matrices for use as a plant tissue cassette or a receiver of a system.

The dimensions of a tissue support matrix can vary depending upon the plant development stage for which the matrix will be utilized as well as the type of plants to be propagated by the system. For instance, FIG. 2 illustrates three different tissue support matrices that can be utilized in a system. In general, the tissue support matrix utilized in initial stages can have a relatively small profile, as the plant material in these stages is primarily heterotrophic and the plantlets can be quite small. As such, use of a smaller support matrix can provide cost savings. This is not a requirement, however, and any suitably sized support matrix can be utilized at any point in the propagation process. For example, and with reference to FIG. 2, a plant tissue cassette 32 for use with early stage heterotrophic plant material can have a smaller profile, for instance about 1 inch or less in height, while a receiver 33, 34 for use later in development as the plantlet becomes more autotrophic and the plant cells begin to differentiate can be larger, having a profile height of about 1 inch or greater, depending on the size of the plantlets and the expected growth of the plantlets during the time they are supported on the particular support matrix.

In one embodiment, a tissue support matrix can be formed of a polymeric foam that can be utilized as a substrate for heterotrophic and/or autotrophic plant growth. This is not a requirement, however, and a support matrix may alternatively be formed of other materials that can provide a rigid or semi-rigid support of fixed dimension. For instance, a tissue support matrix may be formed of a natural material that can be held in a cohesive fashion by use of a natural or synthetic binder. Examples of natural materials include mineral wool materials, such as rockwool or glass wool or Jiffy® Preforma® plant plug system, which is formed of a natural material and adhered with a synthetic polymer.

A tissue support matrix can be formed of a composite that can include an open-celled foam composition in conjunction with other support materials. For instance, a tissue support matrix can be at least in part formed of a phenolic, polyurethane, latex, urea-formaldehyde, or polyisocyanurate-based homopolymer or copolymer foam, with a phenolic-based foam being utilized in one embodiment.

A tissue support matrix can include a foam or other natural porous material in conjunction with one or more filler materials, such as peat.

Materials for use as a tissue support matrix are available on the retail market, for instance from Smithers-Oasis Company of Kent, Ohio. By way of example, Oasis® Horticubes® XL seed propagation medium can be utilized to form a tissue support matrix.

A degradable foam-based tissue support matrix can be utilized in one embodiment as use of a foam support can be conducive to non-contact transplantation of the developing plantlet to a subsequent growth environment. For instance, a single section of a foam-based tissue support matrix (e.g., a single foam cube) can be removed from the remainder of the support and the resulting element can then be located in a new growth environment for a subsequent stage of development.

A degradable support material may also avoid potentially damaging interaction with the developing plant material. For instance, a non-degradable support matrix may require physical separation of the matrix material from the roots of a developing plantlet during transplanting. This can cause root damage and can make transplanting more difficult and less successful. A foam-based tissue support matrix such as the Horticubes® XL foam product can be transplanted in conjunction with the developing roots (in the case of a degradable foam matrix) or can be broken away from the young roots (in the case of a non-degradable or degradable foam matrix), allowing the roots to be washed free of growth medium without damage to the roots.

A tissue support matrix can generally maintain dimensional stability at least through the phase during which the matrix will support the developing plant material. In addition, a tissue support matrix can generally be self-supporting and rigid or semi-rigid. In one embodiment, a tissue support matrix can be absorbent and can also have water holding capacity, in that it is capable of releasing water as well as absorbing it, making water available to the plant.

In one embodiment, a tissue support matrix can be capable of withstanding conditions encountered during sterilization, such as by autoclaving. One advantage of a foam-based tissue support matrix is that it has a cellular structure that can provide air porosity aiding in the exchange of oxygen to the developing root structure.

Referring again to FIG. 1, the plant tissue cassette 30 can be capable of supporting the explant tissue 36 obtained from the tissue source in support areas 35. The explant tissue 36 can be supported for a period of time during which the plant material is generally heterotrophic and the cells of the plantlet are cultivated to grow and multiply. As better seen in FIG. 3, a plant tissue cassette 30 can include a plurality of support areas 35 capable of supporting plant material (e.g., transformed callus) in a liquid growth medium. In this particular embodiment each support area 35 is inset from the surface of the plant tissue cassette 30. While this is not a requirement for a plant tissue cassette, it may be beneficial as it may help to isolate individual plantlets from one another during cultivation.

In general, an individual support area 35 of a plant tissue cassette can be about 2 centimeters or less in diameter, and the support areas 35 can be separated from one another, for instance by a distance of about 2 centimeters or more, so as to maintain isolation of the individual tissue events during the growth and development of the plantlets while supported on the plant tissue cassette 30.

Figure 3:
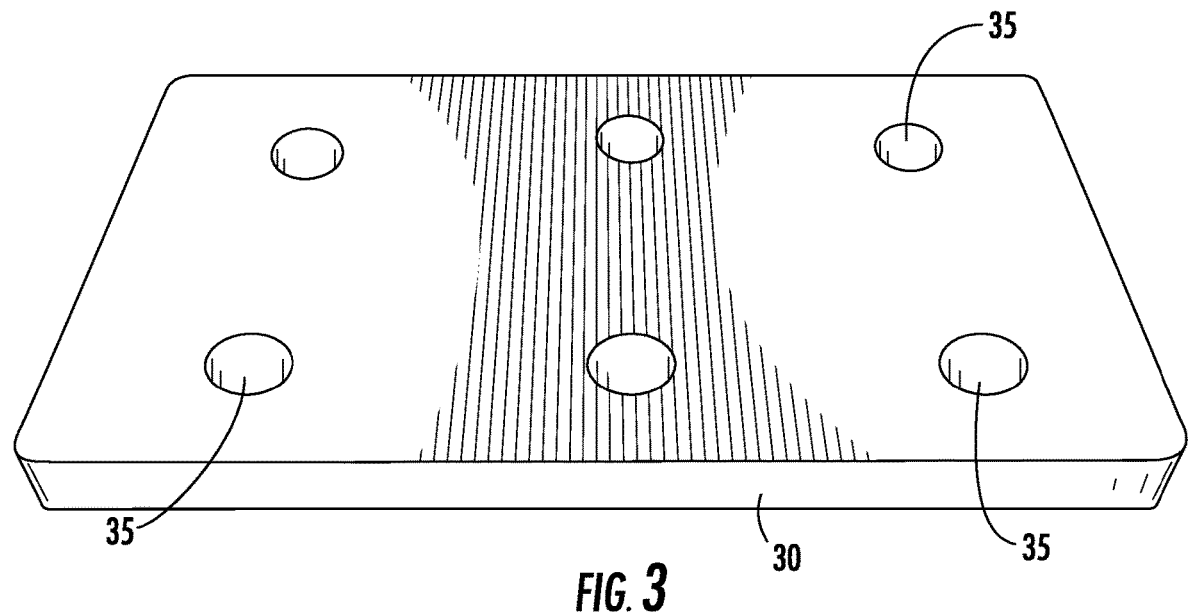
FIG. 3 illustrates one embodiment of a tissue support matrix.

For instance, a plant tissue cassette 30 can be designed with a plurality of individual support areas 35 as shown in FIG. 3, each of which can support a developing plant.

As illustrated in FIG. 1, following a period of time of cultivation on the plant tissue cassette 30, selection of well-formed regeneration events can be carried out followed by transfer of the developing tissue to a receiver 40 for a subsequent growth stage 3 during which the plant material can differentiate and shoots, buds, roots, etc. can begin to form. Beneficially, and as discussed in further detail below, in one embodiment the selected events can be moved from the plant tissue cassette 30 to the receiver 40 in a non-contact fashion and while maintaining polarity of the developing plantlets.

Figure 4:
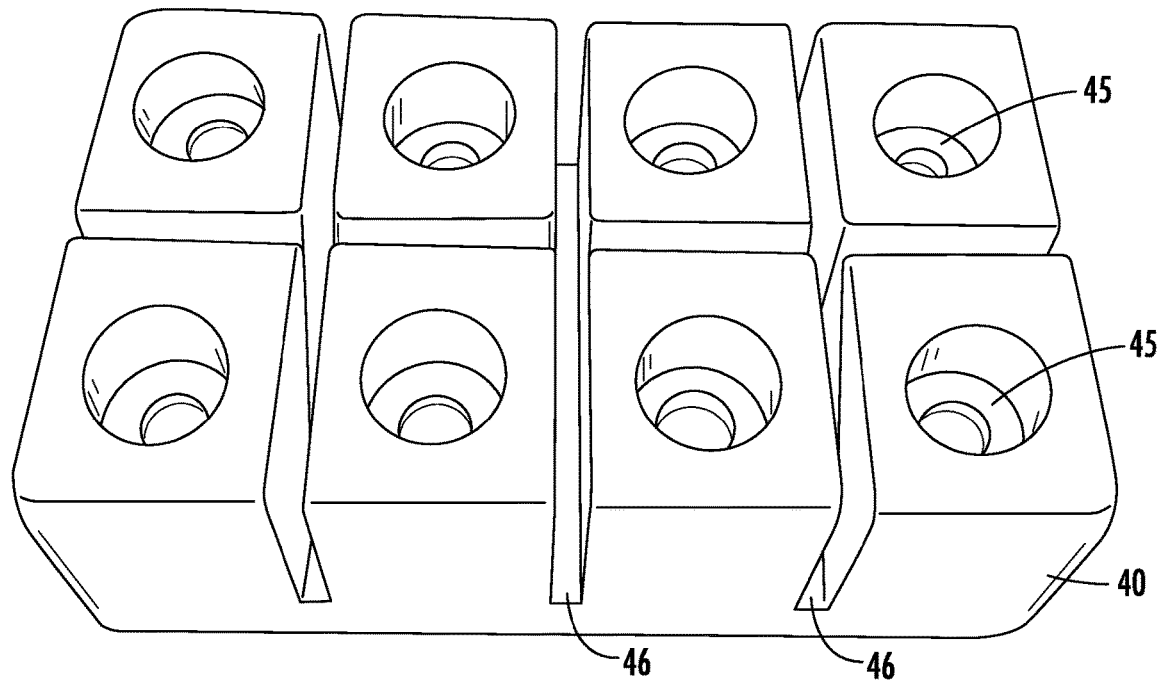
FIG. 4 illustrates another embodiment of a tissue support matrix.

FIG. 4 illustrates one embodiment of a receiver 40. A receiver 40 can be formed of the same tissue support matrix materials as the plant tissue cassette 30 of the system or of different materials, as desired. For instance, in one embodiment both the receiver 40 and the plant tissue cassette 30 can include degradable polymeric foam.

A receiver 40 can generally have a higher profile as compared to a plant tissue cassette 30, as the receiver 40 is designed to support the developing plantlets as they differentiate and grow larger. For instance, in one embodiment a receiver 40 can support developing plantlets up until the plant materials are ready for transplantation into soil, for instance in a greenhouse.

As shown, the receiver 40 includes a series of receiving areas 45, each of which is of a size to support developing plant material in a liquid growth medium. The receiving areas 45 can be separable from one another, which can aid in transplant of the plantlets following initial development utilizing the disclosed system. For instance, in the illustrated embodiment of FIG. 4, the receiving areas 45 can be separated from one another by a score 46, along which the receiving areas can be broken, cut, pulled apart, etc. at the time of transplant. In addition, each receiving area 45 can be inset from a surface of the receiver 40, and the plant tissue can be located on the receiving area 45 and within the inset during growth and development.

Upon suitable maturation of the plant material on the receiver 40, individual receiving areas 45 of the receiver can be separated from one another and each plant separately transplanted to a desired growth medium. For instance, and depending upon the particular material utilized in forming the receiver 40, an individual receiving area 45 that is formed of a degradable material can be rinsed to remove any potentially detrimental liquid growth media, and the entire receiving area 45 that carries the young plant can be located in soil for maturation of the young plant. Alternatively, a young plant can be physically separated from the receiving area, rinsed as necessary to remove any potentially detrimental materials (e.g., sugar from a liquid growth medium) and located in the subsequent growth medium (e.g., soil).

It should be understood that while the process illustrated in FIG. 1 includes 4 stages of development, additional tissue support matrices for use in additional growth stages, each of which can encompass different growth media, etc., is encompassed in a micropropagation process as disclosed herein. For instance, following a period of cultivation on a plant tissue cassette in a first liquid growth medium, developing plant material can be transferred to a first receiver for a period of cultivation in conjunction with a second liquid growth medium. Following this period, the developing plant material can then be transferred to a second receiver for a period of cultivation in a different liquid growth medium and then finally transplanted to soil.

While use of liquid growth media in early stage plant development is not required in the disclosed processes, liquid medium can be utilized rather than more commonly utilized agar in some embodiments, as use of liquid growth media can provide improved ability to combine the liquid growth media with structurally functional matrices that facilitate materials handling (e.g., friable foam matrices). In addition, liquid growth media can better provide for the ability to replenish or remove medium without disturbing the developing plant tissue.

In conjunction with the tissue support matrices, a system can include containers that can be utilized for storage and transport of the tissue support matrices (e.g., prior to location of plant material on the matrices) as well as in some embodiments for holding the tissue support matrices and plant material in conjunction with a liquid growth media during cultivation of the plant material. A container can be a rigid or non-rigid construction, and can be formed of a transparent or opaque material, with a preferred construction of the container generally depending upon the particular application of the container. For instance, if the container is to be used for only transport and storage, a rigid and opaque container may be suitable. If, however, the container is to be used to contain the tissue support matrix during cultivation, it may be beneficial to utilize a transparent container that can allow for light transmission and inspection of the developing plant material.

Figure 5:
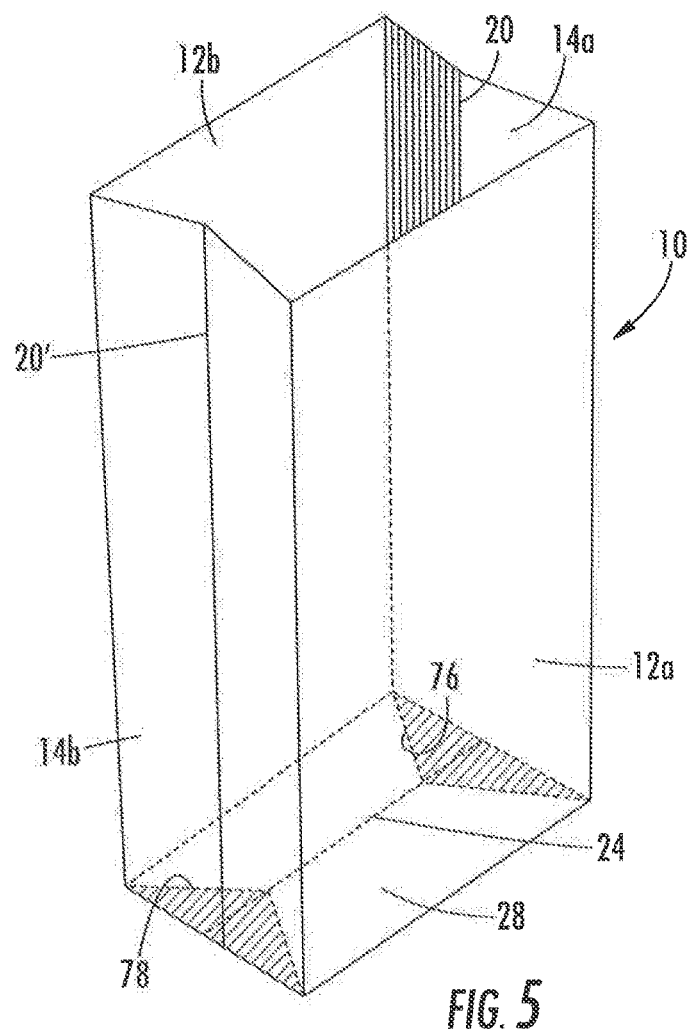
FIG. 5 illustrates one embodiment of a flexible container as may be utilized in conjunction with a tissue support matrix.

FIG. 5 illustrates one embodiment of a container 10 as may be utilized in a system in conjunction with a tissue support matrix. The container 10 is shaped to include a front wall 12a, a back wall 12b, a first side wall 14a, and a second side wall 14b. Though illustrated with a rectangular cross section, this is not a requirement of containers of the disclosed systems, and other cross sections such as square, oval, round, etc. are encompassed herein. The container 10 also includes a base 28 that has a generally flat outer surface in order that the container 10 is capable of self-standing when placed on the base 28. For example, gusset 76 and gusset 78 can be provided on each side of the base 28 to hold the base 28 in a flat orientation at the outer surface of the base 28. The surface area of the base is not particularly limited, and can be of a size such that the system can be stable when in use. For instance, the container base 28 can have a surface area of from about 2 square centimeters ($cm^2$) to about 500 $cm^2$, from about 10 $cm^2$ to about 450 $cm^2$, from about 25 $cm^2$ to about 300 $cm^2$, or from about 50 $cm^2$ to about 200 $cm^2$. Likewise, the internal volume of the container 10 can vary. For example, the container 10 can have a total internal volume of from about 10 $cm^3$ to about 1 $m^3$, from about 50 $cm^3$ to about 5000 $cm^3$, from about 100 $cm^3$ to about 3000 $cm^3$, or from about 500 $cm^3$ to about 2000 $cm^3$.

Container 10 can include fold lines 20, 20' on each side 14a, 14b, as well as a fold line 24 on the base 28. Fold lines 20, 20', 24 can allow for convenient storage of the container when not in use as the container can be folded and stacked with other containers prior to being loaded with a tissue support matrix.

In one embodiment, container 10 can be formed from a single polymeric member, for instance an extruded tubular polymeric member that can be sealed at one end, for instance along fold line 24 via, e.g., a heat seal or by use of an adhesive. Following, the sealed end of the extrudate can be folded to form gussets 76, 78 according to known methodology. The gussets 76, 78 can then be adhered to the base 28, for instance by a heat seal or alternatively by use of a suitable adhesive. When an adhesive is used in formation of the container 10, the adhesive should be one that can withstand any sterilization procedures, and one that will not damage plant material held in the container, e.g., leaching of the adhesive into growth media held in the container during plant development.

The container 10 can be semi-permeable while being impermeable to biological contaminants. In one embodiment, the container 10 can be formed of a single polymeric member that is semi-permeable. In another embodiment, multiple different materials can be used in forming the container 10, one or more of which can be semi-permeable.

A container 10 can be flexible. For instance, one or more of the walls 12a, 12b, side walls 14a, 14b, and base 28 of container 10 can be formed of a flexible material that can be transparent to light necessary for plant growth, liquid impermeable, and impermeable to biological contaminants. Thus, plant material held on a tissue support matrix within the container 10 can receive light and respiratory needs of the developing plant tissues can be met when the container is sealed, and the plant material can be simultaneously shielded from pathogenic microorganisms. For instance, the container can allow for the passage and diffusion therethrough of light rays having a wavelength of from about 400 nanometers (nm) to about 750 nm. Wavelengths in this range are required by individual photosynthetic agents such as the chlorophylls in green tissue plants to provide the reactions necessary for life and growth. Of course, other light wavelengths are also encompassed herein.

The container can be liquid impermeable while allowing for respiration of the developing plant material held within the container. For example, in one embodiment, the container 10 can have a permeability to carbon dioxide ($CO_2$) that is equal to or greater than about 100 cubic centimeters (cc) per 100 square inches ($in^2$) per 24 hours (h) at 1 atmosphere (atm) pressure or greater. For example, the $CO_2$ permeability can be from about 200 to about 1200 cc/100 $in^2$/24 hours at 1 atm. The container can have a permeability to oxygen ($O_2$) of equal to or greater than about 100 cc/100 $in^2$/24 hours at 1 atm, for instance from about 100 to about 450 cc/100 $in^2$/24 hours at 1 atm. The moisture vapor transmission rate (MVTR) of the container can generally be equal to or less than about 1 gram (g)/100 $in^2$/24 h at 1 atm. For example, the MVTR can be from about 0.2 g/100 $in^2$/24 hours at 1 atm to about 0.7 g/100 $in^2$/24 hours at 1 atm.

To shield plant material held in the container from pathogenic organisms, the container can have a porosity that can allow for gas transmission but physically block pathogenic microorganisms from entry. For example, the walls 12a, 12b, 14a, 14b, and base 28 can have an average pore size of about 0.2 micrometers (μm) or less, about 0.1 μm or less, or about 0.05 μm or less, for preventing the passage of pathogenic microorganisms.

The thickness of flexible walls 12a, 12b, 14a, 14b and base 28 can vary, but can generally be from about 1.0 mil to about 4.0 mils, for instance about 2.0 mils. If a flexible material used in forming the container 10 is thinner than about 1.0 mil, handling of the container may be more difficult, as the material may adhere to itself or other materials of the container 10. By use of a relatively thin, translucent material to form at least the walls of a container, the container can have excellent clarity to permit viewing of plant material held on a tissue support matrix enclosed in the container. For example, the walls of a container may be thin and translucent as compared to walls of glass containers. The thicker structure of a glass container can hinder visibility, which can affect decision making regarding plant care as well as complicating the storage and transport of heavier, bulkier containers.

A container 10 can be capable of withstanding a sterilization procedure. For instance, a container 10 can be resistant to high temperature and high pressure sterilizing treatments such as autoclave treatment conditions including subjection to high pressure saturated steam at temperatures of from about 120° C. to about 140° C. and at a pressure of from about 15 pounds per square inch (psi) to about 30 (psi).

By way of example and without limitation, a high density polyethylene or a polypropylene can be utilized to form a container 10. For instance, a polyethylene having a density of from about 0.93 $g/cm^3$ to about 0.97 $g/cm^3$ can be utilized in forming a container. In one embodiment, the container can include a biaxially oriented polypropylene.

A biaxially oriented polypropylene is one that is stretched in both the machine and cross directions so as to increase the strength and clarity of the material. According to one embodiment, a sequential biaxial orienting method can be utilized to form a film that forms a container 10. Briefly, pellets or chips of a polypropylene resin can be supplied to an extruder and then heated and melted at a temperature of from about 170° C. to about 320° C. The melt can be extruded from a die and then cooled and solidified, for instance on a metal drum held at a temperature of from about 60° C. to about 140° C. to obtain a cast raw sheet with β-form crystals. Next, the cast raw sheet can be made to pass between rolls rotating at different rates while maintaining the temperature of the cast raw sheet from about 100° C. to about 160° C. to stretch the cast raw sheet in the flow direction and gain, e.g., a three- to seven-fold length increase. After that, the resultant sheet can be cooled. Following, the cooled sheet can be directed to a tenter, and stretched in the width direction to gain, e.g., a three- to eleven-fold width increase while keeping the temperature of the sheet at about 150° C. or more. Finally, the resultant biaxially oriented sheet can be relaxed and subjected to thermal fixing, followed by winding and further processing, for instance formation of a container 10.

Figure 6:
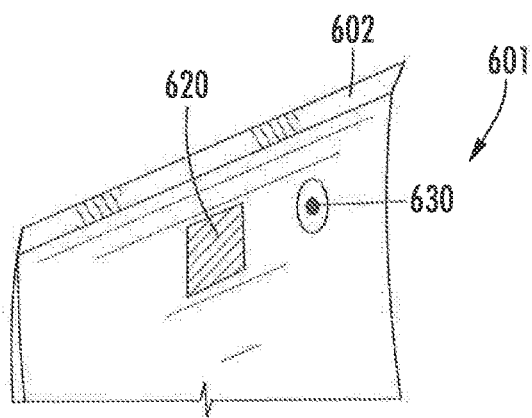
FIG. 6 illustrates one embodiment of the seal portion of a flexible container.

The container can optionally include a vent in a wall. For example, container 601 illustrated in FIG. 6 includes a gas diffusion membrane vent 620 that can facilitate diffusion of gases from the outer surface of the container to the inner space of the container. Of course, the gas diffusion membrane vent 620 can have any suitable shape including round, oval, rectangular, etc. and is not limited to a square vent 620 as illustrated in FIG. 6. During use, oxygen, nitrogen, carbon dioxide, etc. can pass through the vent 620. The membrane vent 620 can be formed of materials similar to those of the container walls, with the difference in that the membrane vent 620 allows a larger diffusion of gases as compared to the container. For example, the membrane vent 620 can be formed of a high density polyethylene or a polypropylene that is liquid impermeable and impermeable to pathogenic agents with an increased permeability to oxygen and carbon dioxide as compared to the remainder of the container 601.

The container 601 can also be formed such that sealed edge 602 may be folded over the membrane vent 620 to better control the gas diffusion characteristics of the system. For example, after the desired plant tissue has been located within the system, the system may be filled with the correct gasses for healthy plant growth and sealed with little or no flow allowed through the membrane vent 620.

Figure 7:
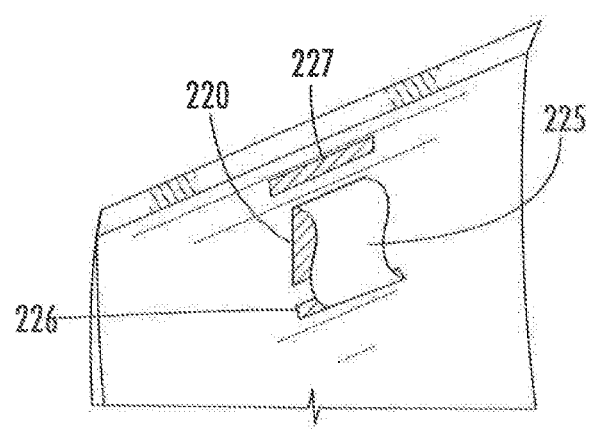
FIG. 7 illustrates one embodiment of the seal portion of a flexible container.

Alternatively, a vent 620 may be open throughout use of the device with no closure or may have a separate closure. For instance, in the embodiment illustrated in FIG. 7, the container can include a vent 220 that incorporates a closure 225. As can be seen, closure 225 is in the form of a flexible flap that can overlay the vent 220 as desired to effectively close the vent 220 and prevent diffusion through the vent 220. In this embodiment, closure 225 can be attached to the container when vent 220 is to be closed as with adhesive strip 226. The container can also include a second adhesive strip 227 that can be used to hold the closure 225 such that the vent 220 is uncovered and open.

During certain times of development of plant tissue held within the system, the membrane vent 220 can be uncovered and the developing plant tissue can receive additional gasses in a controlled environment. For example, utilization of a membrane vent can reduce the development of hyperhydricity in the growing plants. During transport of the system the vent can be closed, e.g., covered by the closure 225 or some other device to avoid gas exchange between the container interior and the surrounding environment during transport.

In one embodiment, illustrated in FIG. 6, the container 601 can include a vent 620 and a port 630 near the sealable top 602 of the container 601. The port 630 can be utilized to inject or remove gases into or out of the container 601. This may be utilized to control pressure within the container 601 as well as to control the gaseous contents of the container 601 during growth and development of the plant material held within the system. For instance, following a period of growth and development, an amount of the gases inside the container can be removed so as to remove excess oxygen from the container, and gas higher in carbon dioxide can be injected through the port 630. A port can be, for instance, a one-way injection port that can be utilized with a syringe or the like.

Figure 8:
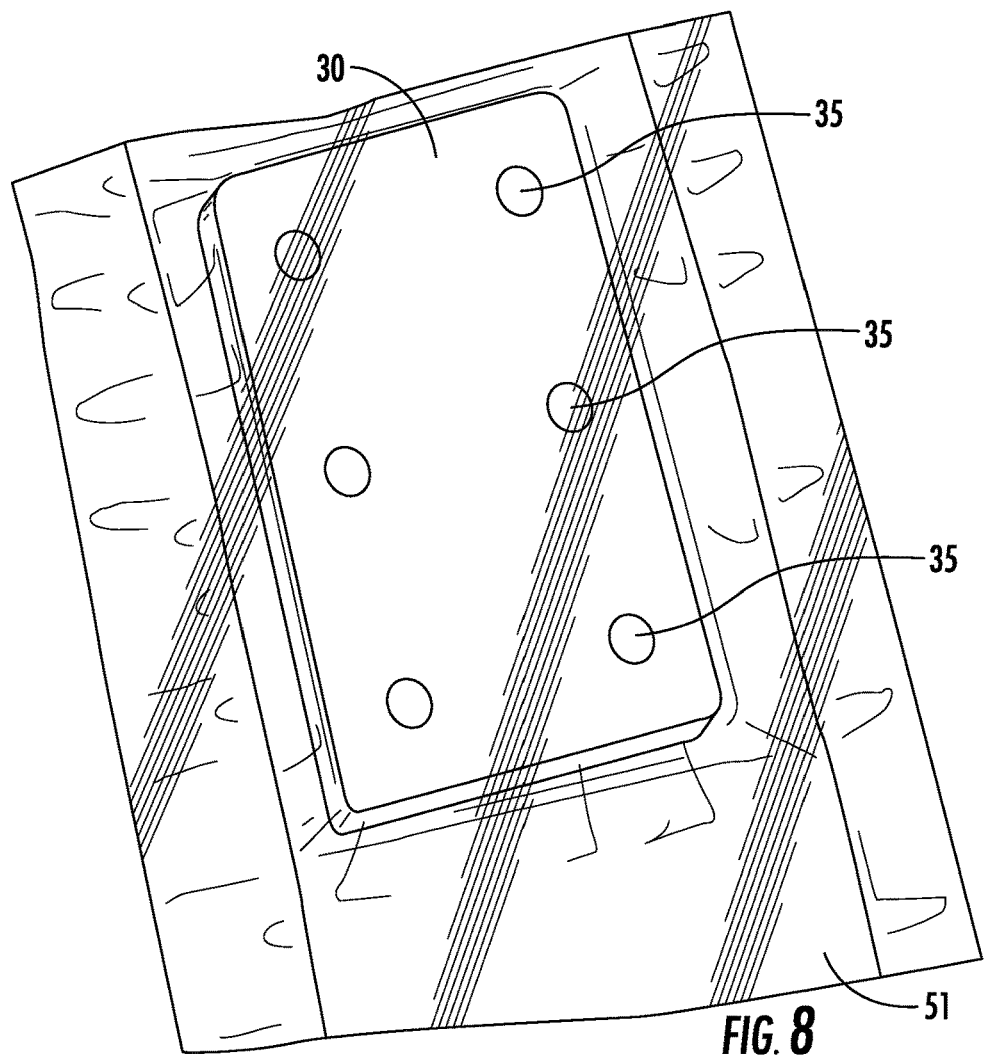
FIG. 8 illustrates one embodiment of a tissue support matrix held in a sterilizable container for storage or transport.
Figure 9:
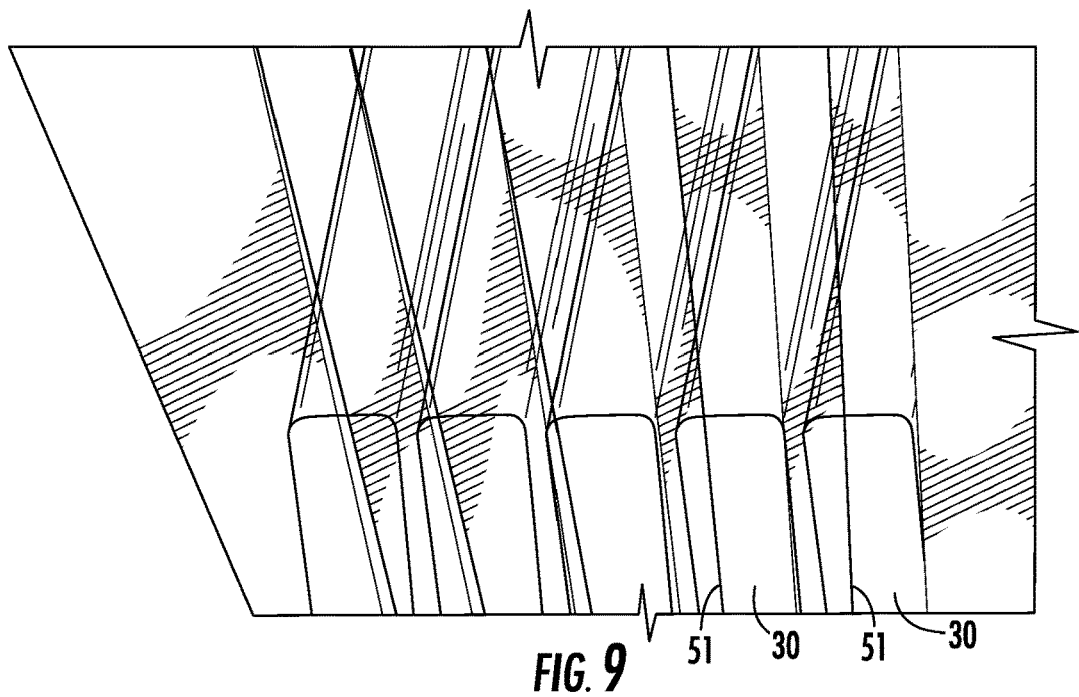
FIG. 9 illustrates a series of tissue support matrices each held in a sterilizable container for storage or transport.

A container can be utilized for storage and transport of a tissue support matrix. For instance, as illustrated in FIG. 8 a plant tissue cassette 30 can be sealed within a flexible polymeric container 51 following sterilization for storage and/or shipping prior to locating plant material on the support areas 35 of the plant tissue cassette 30. As shown in FIG. 9, a plurality of plant tissue cassettes 30, each held in a separate container 51 can be conveniently stacked together for shipping and/or storage prior to use.

A tissue support matrix (i.e., either a plant tissue cassette or a receiver) can also be assembled with a container during cultivation of plant material while supported on the matrix. For instance, and with reference to FIG. 8, at the time of use, the container 51 can be opened and plant material located on the support areas 35 of the tissue support matrix 30. Depending upon the nature of the container 51, the container can then be resealed for the period of time that the plant material is cultivated on the tissue support matrix 30 or alternatively can be held open to the atmosphere during the cultivation period.

In one embodiment, a system can include a water impermeable container and as such an exterior of the container may be intermittently misted without diluting the growth media held in the container. Upon misting, the evaporation of water from the container's exterior surface can help to control the interior temperature of the system (for instance when the containers are utilized in a greenhouse).

Figure 10A:
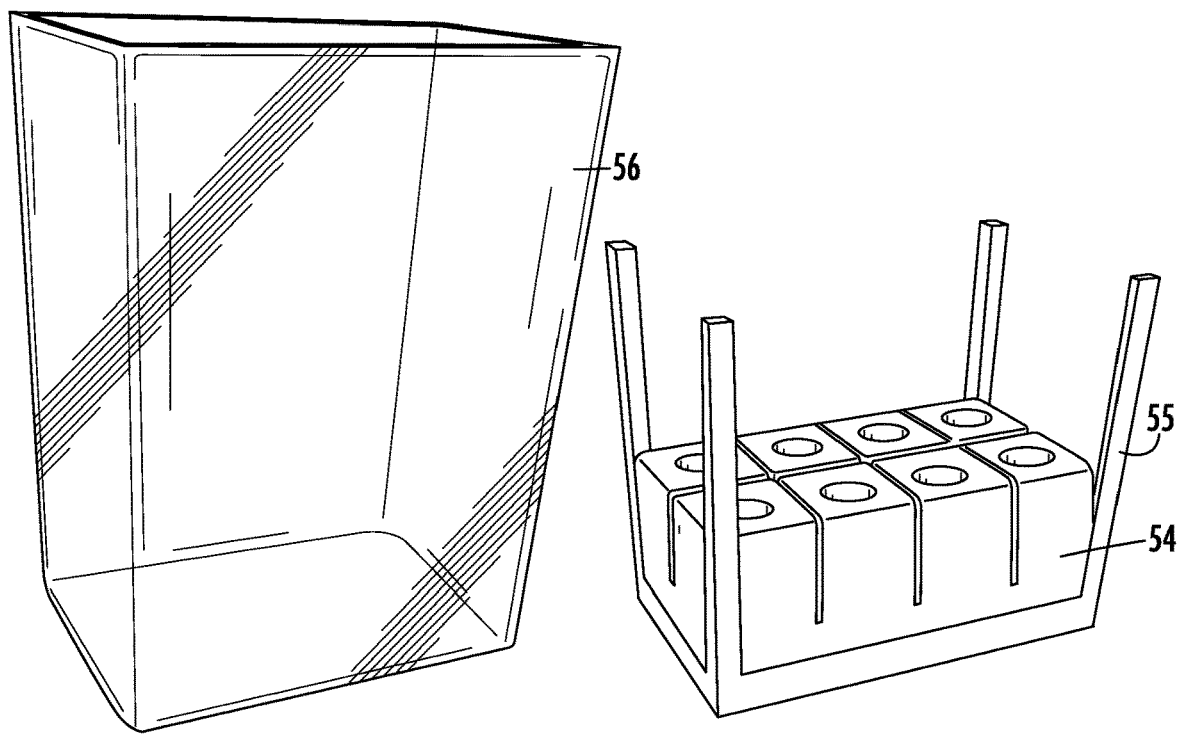
FIG. 10A, FIG. 10B and FIG. 10C illustrate one embodiment of a method for placing a tissue support matrix in a flexible container.
Figure 10B:
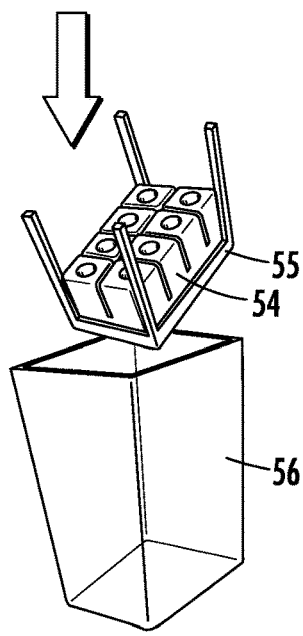
Figure 10C:
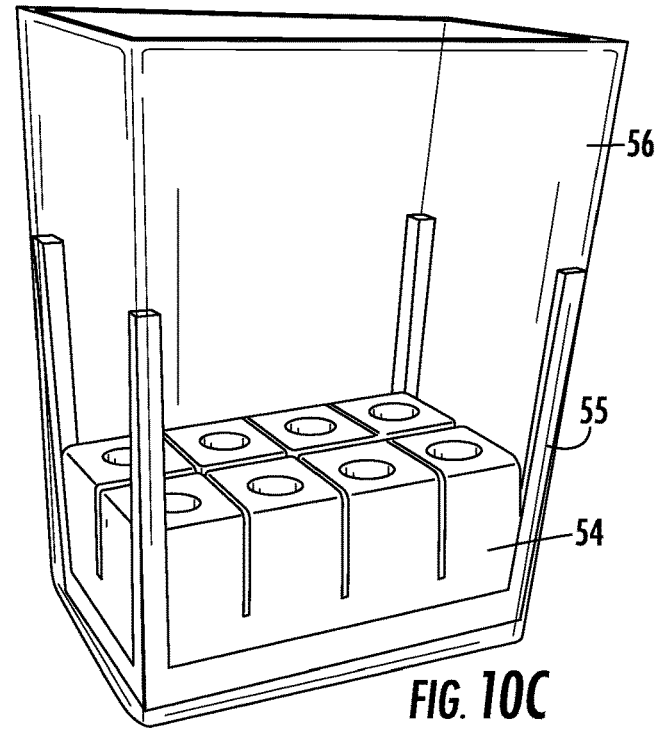

FIG. 10A, FIG. 10B, and FIG. 10C illustrate a method for assembling a tissue support matrix 54 with a flexible polymeric container 56. In this embodiment, the system also includes a support 55 that allows for hands-free manipulation of the support matrix 54 and can also provide for some additional structural support of the tissue support matrix 54 after it has been placed within the container 56.

Upon assembly (FIG. 10C), a system can include a tissue support matrix 54 held within a container 56. The container 56 can be sized so as to generally fit the dimensions of the tissue support matrix 54, which can improve stability of the system as well as prevent distortion of the container 56 during sterilization of the system. The support 55 that can also function as a transfer strut as shown, can help to maintain a headspace over the developing plant material, which can be of benefit, for instance for correct vertical development of leaf and tillers during later stages of development (e.g., when the developing plant material is supported on a receiver).

The components of a system can be sterilized prior to loading plant material onto a tissue support matrix. For instance a tissue support matrix and a container can be sterilized either prior to or following assembly with one another by use of an autoclave, according to standard practice. By way of example, an autoclave sterilization process may be utilized during which the autoclave may reach a temperature of about 250° F. (about 120° C.) at a pressure of about 15 psi.

To utilize the system, a plant material that is heterotrophic and that can include dedifferentiated callus or undifferentiated meristematic cells can be located on a support area of a plant tissue cassette. The plant material located on a plant tissue cassette can include, for instance, transformed tissue, a somatic embryo, a zygotic embryo, tissue developed from an embryo, or any viable heterotrophic unit of living plant material containing totipotent cells capable of growing under controlled conditions into a complete autotrophic plant possessing roots and shoots. One source of such heterotrophic plant material is a liquid culture of plant somatic embryos that can be derived from explanted zygotic embryos of a source plant. This process, such as described by Durzan and Gupta, Plant Science 52:229-235 (1987), involves several culture steps involving different gel and liquid media containing mineral nutrients, organic compounds to supply carbon and energy, specific plant hormones, and water. Other sources of suitable heterotrophic plant material are cultured meristematic tissue, explanted zygotic embryos, cultured bud tissues, totipotent callus tissues, and the like, produced by any of a number of currently practiced plant propagation techniques including micropropagation techniques, somatic embryogenesis, plant regeneration, genetic transformation, and so forth.

An aqueous growth medium can be included in the system either prior to or following location of the plant material on a tissue support matrix, e.g., a plant tissue cassette. Addition of the aqueous growth medium to a container prior to sterilization may be preferable in some embodiments, as the sterilized system can be stored and shipped ready for use, and the end user need only insert the desired plant tissue (e.g., a callus, a microcutting, meristemic cells, etc.) through an opening of the container. The top of a container can be held in a closed arrangement either with a tight seal or a loose closure. For instance, the container top can be closed with a heat seal (see, e.g., FIG. 19) for a tight seal or more loosely, as with a clip, for a loose seal.

A liquid growth medium can generally be any suitable medium as is known in the art, with preferred media depending upon the plants to be developed within the system as well as the growing conditions to be utilized during the time the plants are held in the system. By way of example, a liquid growth media can include, without limitation, one or more of $NH_4NO_3$, $KNO_3$, $H_3BO_3$, $KH_2PO_4$, KI, $Na_2MoO4.H_2O$, $CoCl_2.6H_2O$, $CaCl_2.2H_2O$, $MgSO_4.7H_2O$, $MnSO_4.H_2O$, $ZnSO_4.7H_2O$, $CuSO_4.5H_2O$, pyridoxine nicotinic acid, glycine, sucrose, and so forth. Plant growth media as are known in the art can be utilized such as, for example, micropropagation medium as described by Murashige and Skoog (MS 1962), supplemented with 3% sucrose, organic components as described by Linsmaeier and Skoog (1965), with 1 µM of a plant growth regulator such as meta-topolin. A plant growth media can be at a pH of between about 5 and about 7, for instance at pH 5.7. Of course, desirable pH of a media can depend upon the specific plant tissue to be developed by use of the system.

A medium containing mineral nutrients can be utilized in promoting the growth of the developing plants, but is not necessary in all cases. In addition, the nutrients and carbon and energy source may be mixed in dry powder or particulate form and thereafter water can be added to form the aqueous medium. The term aqueous solution or growth medium thus encompasses a solution formed by adding water to a system that contains dried nutrients and other materials as well as to a solution formed by mixing such materials with water and applying the formed mixture to the system.

An aqueous medium may also include one or more plant growth hormones to stimulate growth and development of plant structures, such as shoots or roots, from the plant tissue supplied to the system. While somatic embryos may have sufficiently developed rudimentary shoot and root so as to not require growth hormones in the medium, other types of heterotrophic plant material may not, such as micropropagated adventitious meristematic tissue, buds, or microcuttings. Hence, depending upon the particular type and state of development of the heterotrophic plant material supported on the plant tissue cassette, the addition of plant hormones such as auxins and cytokinins may be advantageous.

The amount of aqueous media included in a system can vary depending upon the length of time the system is to be utilized, the type of plant to be developed by the system, the particular growing conditions to be utilized, the size of the tissue support matrix (e.g., a plant tissue cassette or a receiver), etc. For example, aqueous media can be included in a system in an amount of from about 0.3 milliliters per cubic centimeter of tissue support matrix ($mL/cm^3$) to about 1 $mL/cm^3$, for instance from about 0.4 $mL/cm^3$ to about 0.9 $mL/cm^3$. Of course, higher or lower amounts are likewise encompassed herein, depending upon the nature of the development process.

After the plant material has been placed on a plant tissue cassette, the container that holds the plant tissue cassette can be sealed, for instance with a heat seal as illustrated in FIG. 6 to form a closed top 602. Once sealed, the system can be conveniently held either alone or in conjunction with other systems for development of the plant tissue held inside as well as for shipping of the plant tissue. For instance, a plurality of the systems can be stacked and packed together for shipping. Upon sealing the top 602, a system can form a stackable shape with the developing plant material protected inside. The combination of a sealed container, which will prevent the gases inside from escaping, and the tissue support matrix held within the container can provide a stable system that can be packed and/or stacked with other such systems without damage to the plant material held inside.

Figure 11:
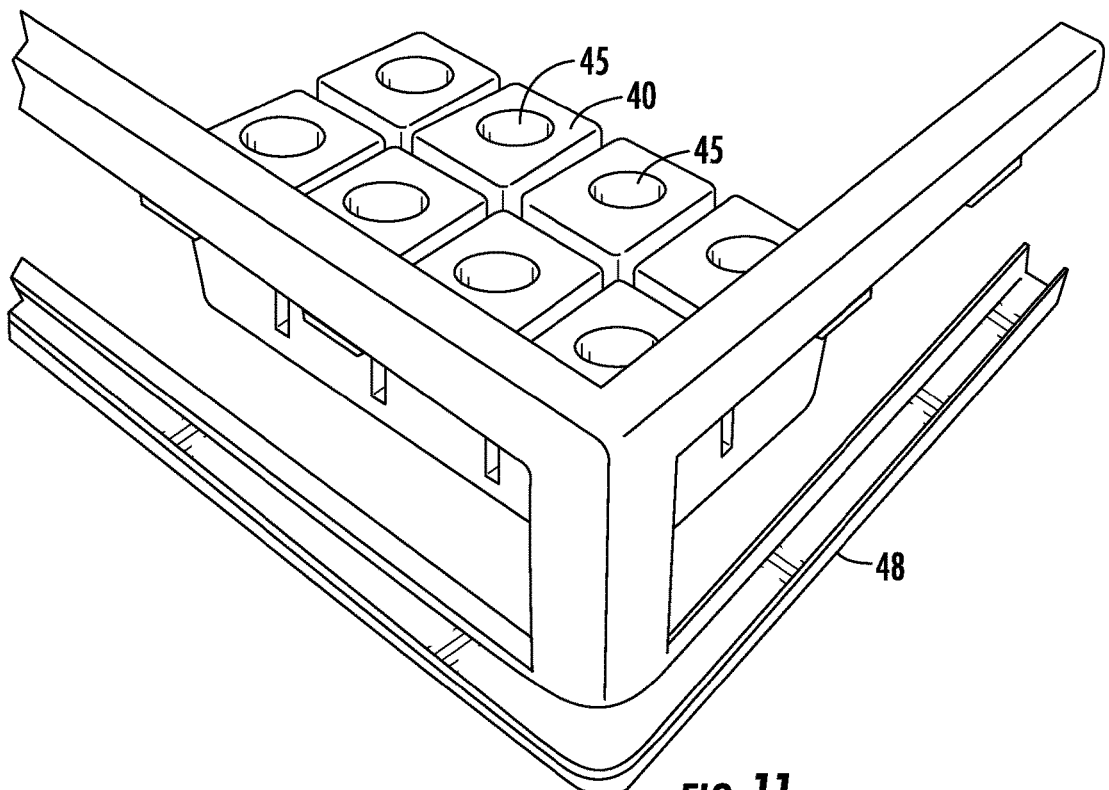
FIG. 11 illustrates one embodiment of an alignment stand as may be utilized with a system as disclosed herein.
Figure 12:
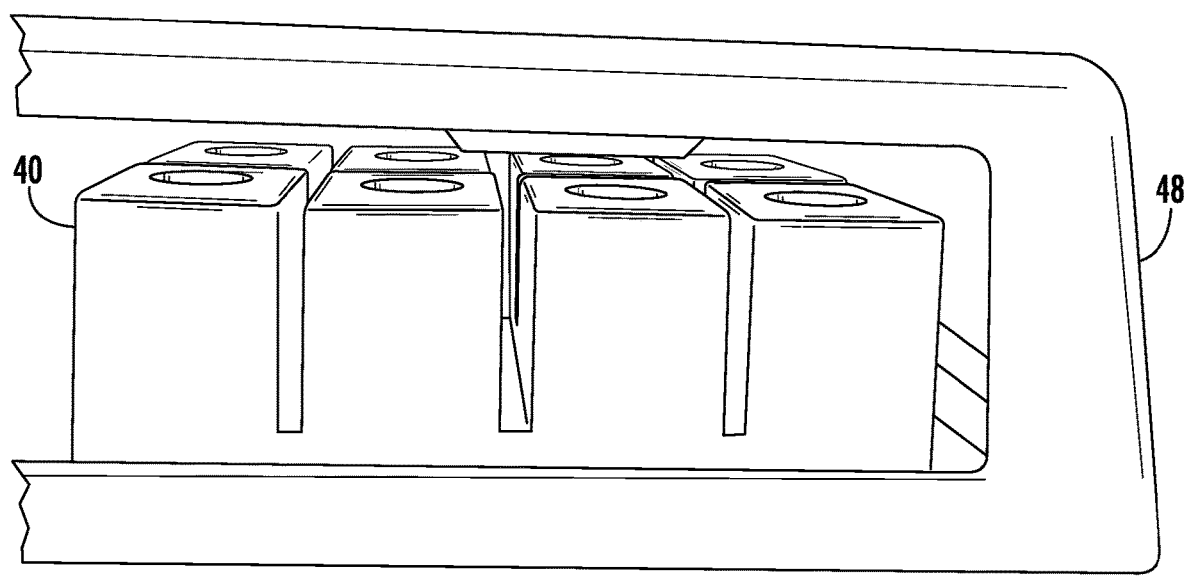
FIG. 12 illustrates a side view of a tissue support matrix as a receiver and held in conjunction with an alignment stand.

Following a period of cultivation, developing plant material can be transferred from a plant tissue cassette to a receiver. FIG. 11 illustrates a perspective view of a receiver 40 prior to transfer of plant material to the receiving areas 45 of the receiver 40. FIG. 12 presents a side view of the receiver 40. In this embodiment, the system also includes an alignment mechanism 48 that can aid in aligning the receiver 40 with a plant tissue cassette that is carrying developing plant material.

An alignment mechanism 48 can have any desirable structure and geometry. For instance, an alignment mechanism can be formed of a molded plastic, as shown, and can align a single plant tissue cassette/receiver pair or can be larger and align a plurality of plant tissue cassette/receiver pairs simultaneously.

Figure 13:
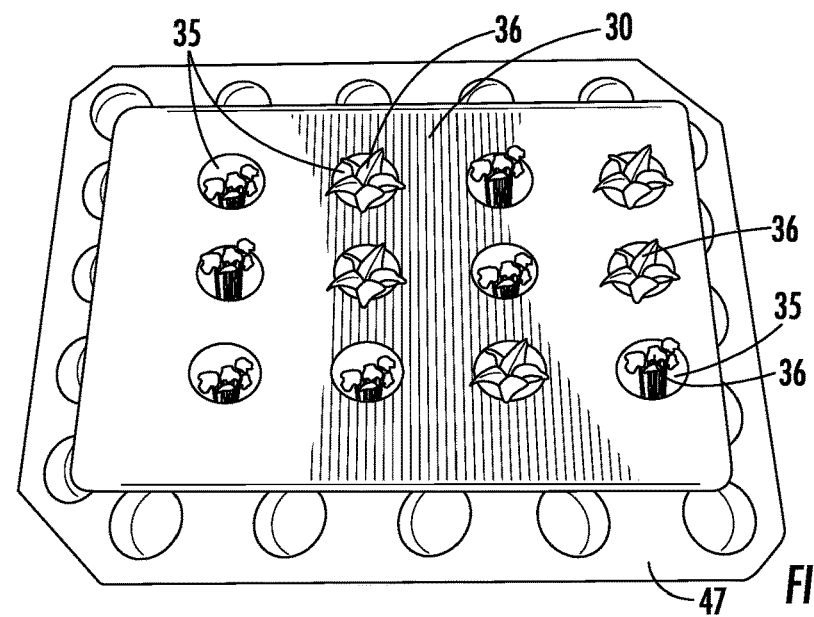
FIG. 13 illustrates a tissue support matrix as a plant tissue cassette and a support plate.

An alignment mechanism can include multiple components. For instance, FIG. 13 illustrates a plant tissue cassette 30 including a plurality of support areas 35 each of which supporting plant material 36. The plant tissue cassette 30 is supported on an alignment plate 47 that is a component of an alignment mechanism 48.

The developing plant material 36 can be moved from the plant tissue cassette 30 at any suitable point during development of the plants. In general, however, a convenient point for transplanting the plant material from the plant tissue cassette 30 to a receiver 40 (or from one receiver to another receiver) can be when the plant material begins to outgrow the individual support areas 35 of the plant tissue cassette 30 and/or when it is desirous to change the liquid growth media of the developing tissue.

Beneficially, the individual support areas 35 of the plant tissue cassette 30 allow for the tissue events to remain mechanically isolated throughout the early stages of development. For instance, the mechanical isolation of events in a tissue support matrix can allow for several transformation events in one vessel without possibility of cross-contamination between the separated events.

Figure 14:
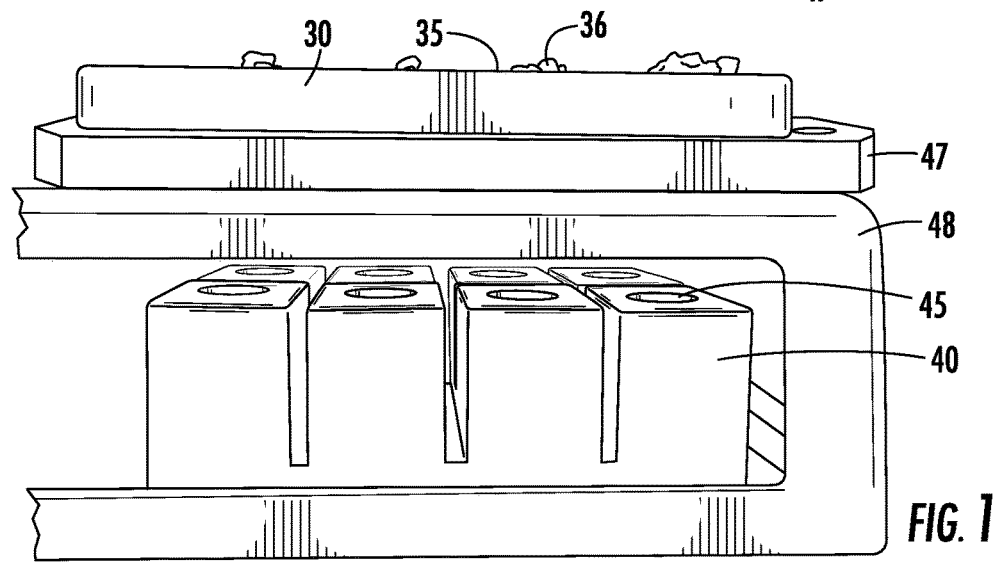
FIG. 14 is a side view of a plant tissue cassette aligned with a receiver by use of an alignment stand and a support plate.
Figure 15:
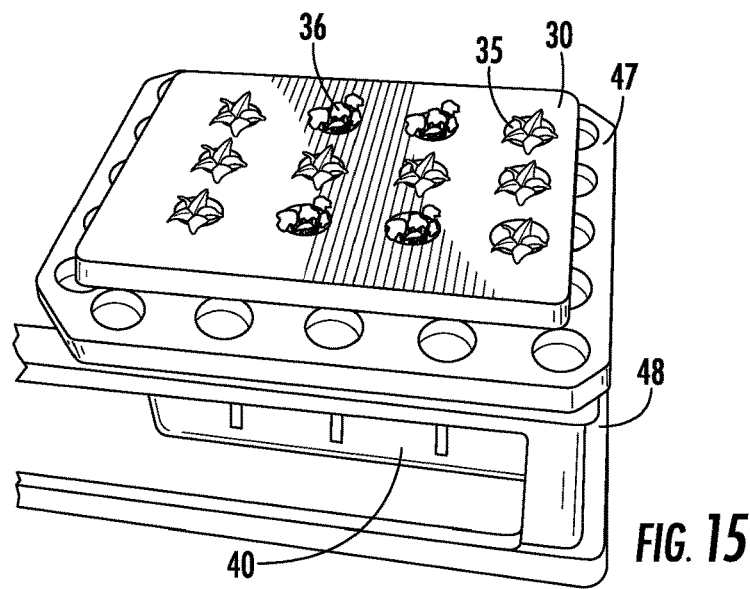
FIG. 15 is a perspective view of a plant tissue cassette aligned with a receiver by use of an alignment stand and a support plate.

As illustrated in FIG. 14 and FIG. 15, an alignment mechanism 48 that in this embodiment includes an alignment plate 47 can be utilized to align the individual support areas 35 of a plant tissue cassette 30 with the receiving areas 45 of a receiver 40. Prior to transfer, the support areas 35 can be carrying developing plant material 36. As shown, the alignment plate 47 can include a series of apertures through which the plant material 36 can be transferred to the receiver 40.

In one embodiment following a period of cultivation of the plant material 36 on the plant tissue cassette 30, the plant material 36 can be transferred from a plant tissue cassette 30 to a receiver 40 in a hands-free fashion (i.e., no contact with the developing plant material). Of course, it should be understood that a hands-free transfer process is not required, and in one embodiment the developing plant material can be transferred from one tissue support matrix to another in a more conventional hands-on manual fashion. However, the use of a hands-free transfer of the plant material can facilitate aseptic selection of desired plant material as well as help to maintain the aseptic nature of growth media and avoid damage to the developing plant material.

Figure 16A:
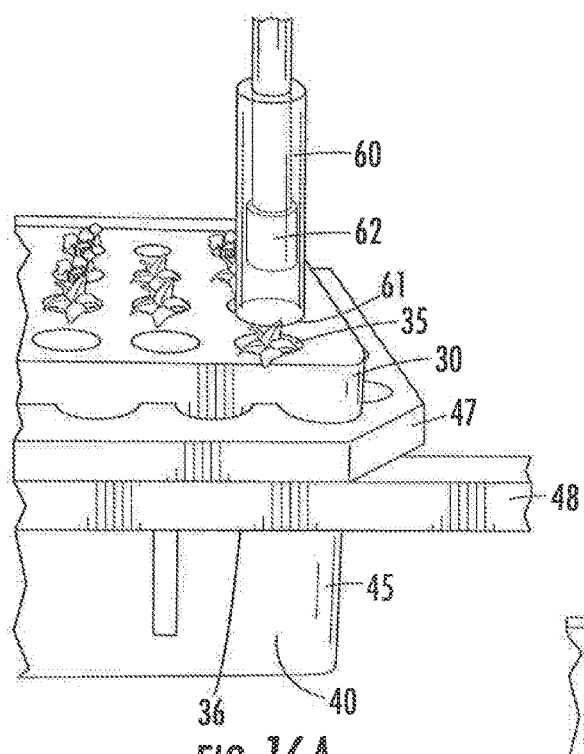
FIG. 16A, FIG. 16B, and FIG. 16C illustrate one embodiment of a method for transplanting plant material from a plant tissue cassette to a receiver by use of a tool.
Figure 16B:
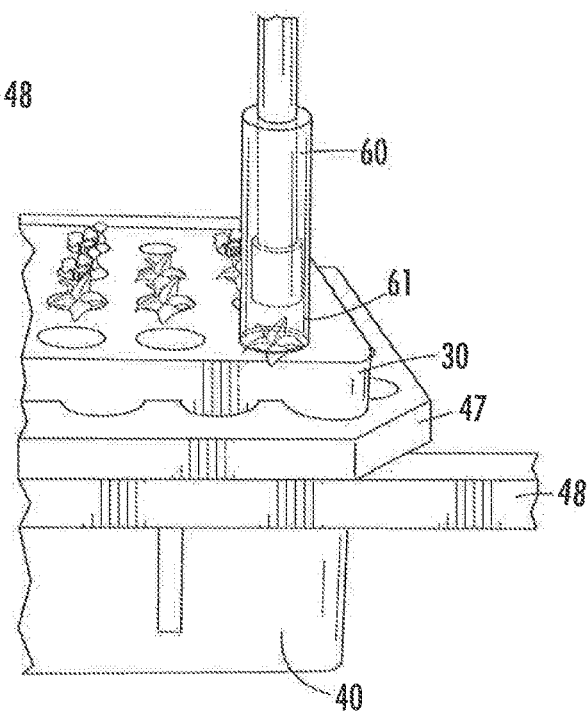
Figure 16C:
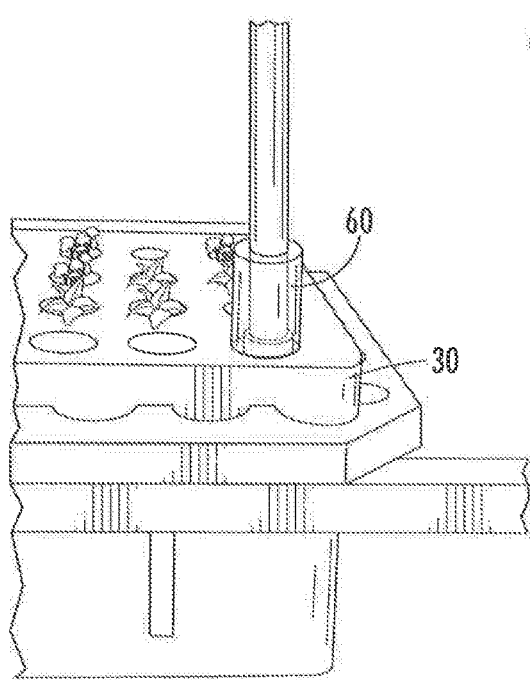

FIG. 16A, FIG. 16B, and FIG. 16C illustrate a hands-free transfer process. In this embodiment, following alignment of a single support area 35 of a plant tissue cassette 30 with a receiving area 45 of a receiver 40 by use of an alignment mechanism 48 that includes an alignment plate 47, a tool 60 can be utilized to separate a single support area 35 away from the remainder of the plant tissue cassette 30 and allow for or actively facilitate transfer of the support area 35 and the plant material 36 thereon to an aligned receiving area 45. It should be understood that a tool 60 can facilitate separation of a single support area from the remainder of a plant support matrix according to any desirable means. For instance and without limitation, a tool can cut, pull, dissolve, lift, rip, or use any other mode of separation or combination thereof to separate a single support area 35 or receiving area 45 from the remainder of a plant tissue cassette 30 or receiver 40, respectively.

In the particular illustrated embodiment of FIGS. 16A, 16B and 16C, the tool 60 can include a cutting edge 61 capable of cutting a support area 35 away from the remainder of the plant tissue cassette 30 without damage to the developing plant material. For instance, in the illustrated embodiment, the tool 60 includes a circular cutting edge 61 and a chamber 62. The cutting edge 61 can be placed against the surface of a single support area 35 with the developing plant material 36 held in the chamber 62 as shown in FIG. 16B. By applying downward pressure to the cutting edge 61, optionally in conjunction with a lateral rotation, the support area 35 can be cut away from the remainder of the plant tissue cassette 30. The downward pressure of the tool 60 can carry the support area 35 and the plant material 36 through an aperture of the alignment plate 47 and to a receiving area 45 of the receiver 40.

Though illustrated as a manually operated tool 60, it should be understood that a tool can optionally be a component of an automated system. This can provide a route for high throughput transfer as well as allow for the operating technician to be at a distance from the event, providing further prevention of possible contamination of the plant material. For example, an automated system can provide for positioning of the tissue support matrices in upper and lower registration by cam mechanism, and an automated tool can transfer one or more individual events from a plant tissue cassette to a receiver in a single step. LCD displays electronic switch actuation, and so forth as are generally known in automated systems can also be included and that can contribute to improved automation of a work station.

Figure 17:
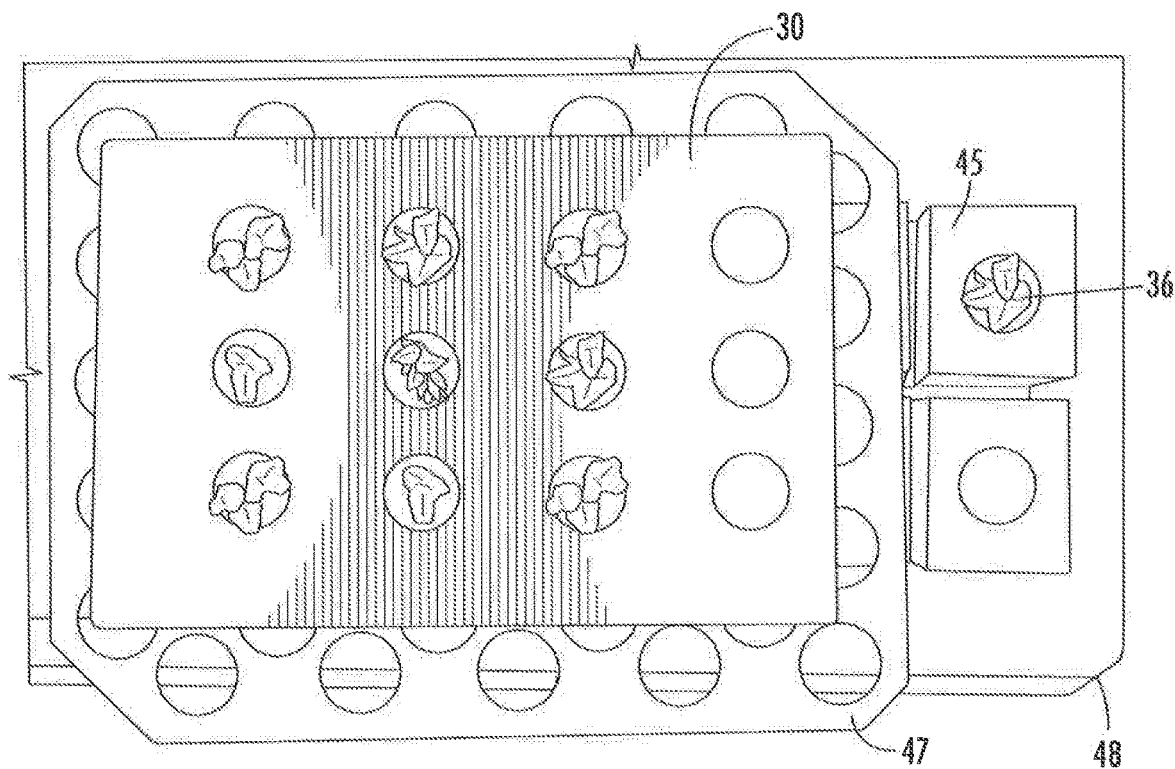
FIG. 17 illustrates a plant tissue cassette, a support plate, an alignment stand and a receiver following transplantation of plant material from the plant tissue cassette to the receiver.
Figure 18:
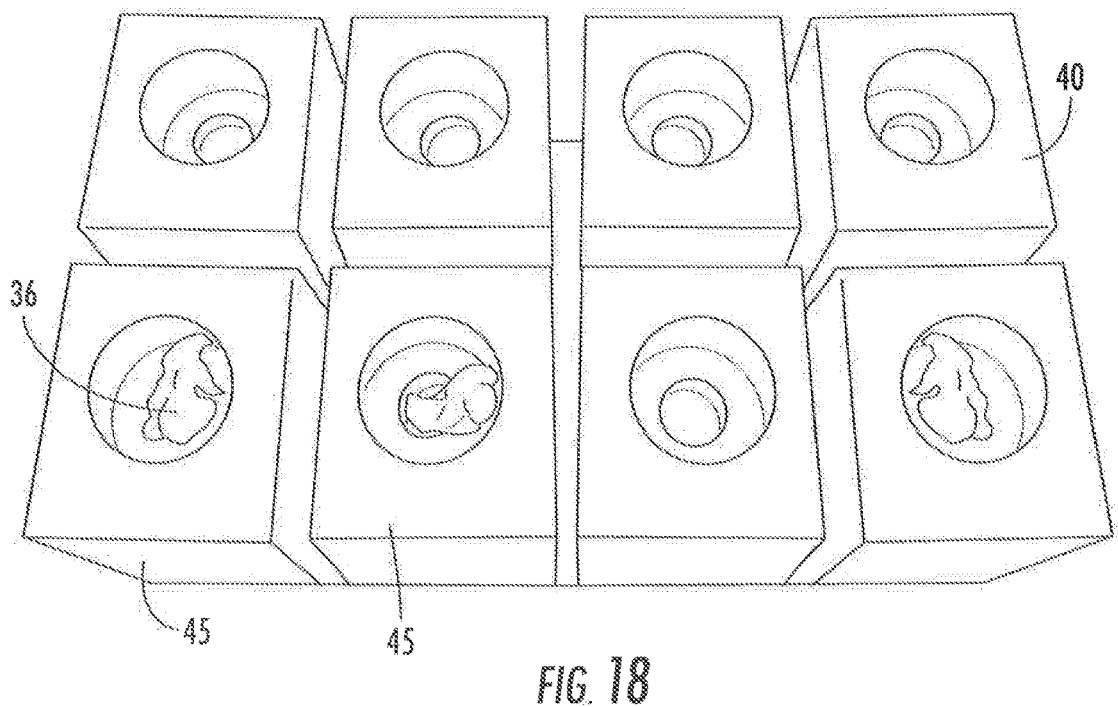
FIG. 18 illustrates a receiver following transplantation of plant material from a plant tissue cassette to the receiver.

FIG. 17 is a top view following transfer of plant material 36 from a plant tissue cassette 30 to a receiving area 45 and FIG. 18 illustrates a receiver 40 following the transfer by use of an alignment mechanism 48 that in this embodiment includes an alignment plate 47. A receiver 40 can be configured to allow a bipolar plantlet to grow to a size and in one embodiment to be developmentally competent for greenhouse transfer. It can be formed of materials as discussed previously for tissue support matrices. In one embodiment, the receiver 40 can include a foam material, which can allow for root growth in which roots are not damaged during later transfer, for instance to greenhouse soil. As can be seen in FIG. 17 and FIG. 18, by vertical transfer of the plant material 36 from the plant tissue cassette 30 to the receiver 40 the integrity of positional information of the developing plant material can be maintained.

Through the individual transfer process, selected events can be transferred from the plant tissue cassette 30 to the larger receiver 40. The receiving areas 45 can be partially saturated with growth medium suitable for the growth stage of the developing plant material, for instance growth medium designed to encourage shoot and root development. For instance, following transfer of dedifferentiated callus from a plant tissue cassette 30 to a receiver 40, differentiation and more controlled growth during maturation phase can occur as the plant material is supported on a receiving area 45 of a receiver 40. In those embodiments in which the receiving area includes a porous support material, the roots of the developing plant can grow into the receiver. Upon subsequent transfer, a single receiving area can be separated from the remainder of the receiver, the receiving area including the plant material can be rinsed free of growth medium, and the degradable receiving area can be transferred to soil without damaging the roots.

Figure 19:
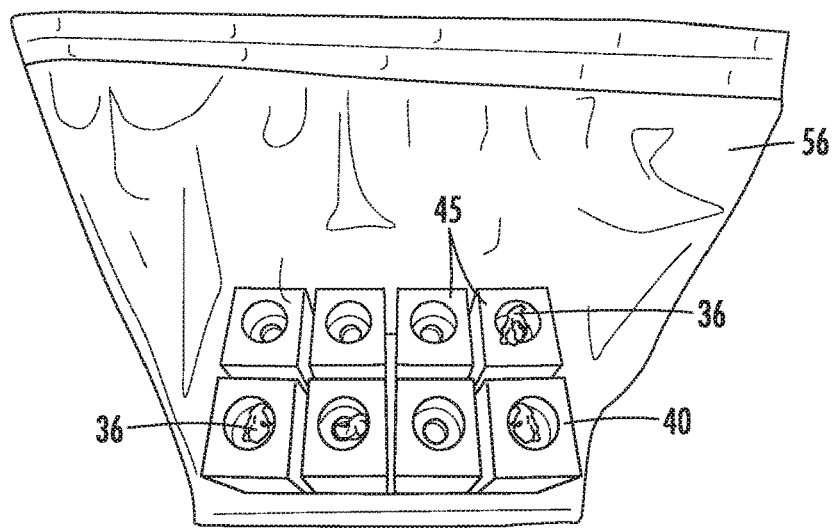
FIG. 19 illustrates a receiver within a flexible container.

By way of example, FIG. 19 illustrates a receiver 40 following transfer of a plurality of plant material events 36 to individual receiving areas 45 that are physically separated from one another. The entire receiver 40 is contained within a container 56 for aseptic isolation of the developing plant material and the growth medium held in the container in conjunction with the receiver 40. In this embodiment, the container 56 is formed of a sterilizable, gas permeable, liquid impermeable polymeric film, as discussed above. The container 56 can allow for light transmission and, in one embodiment, gas permeation, to encourage cell differentiation and plant development. For instance, by use of flexible containers, rooted plants in sealed, clear plastic containers may be shipped to greenhouse and bright light acclimatized while held in the aseptic conditions.

Figure 20:
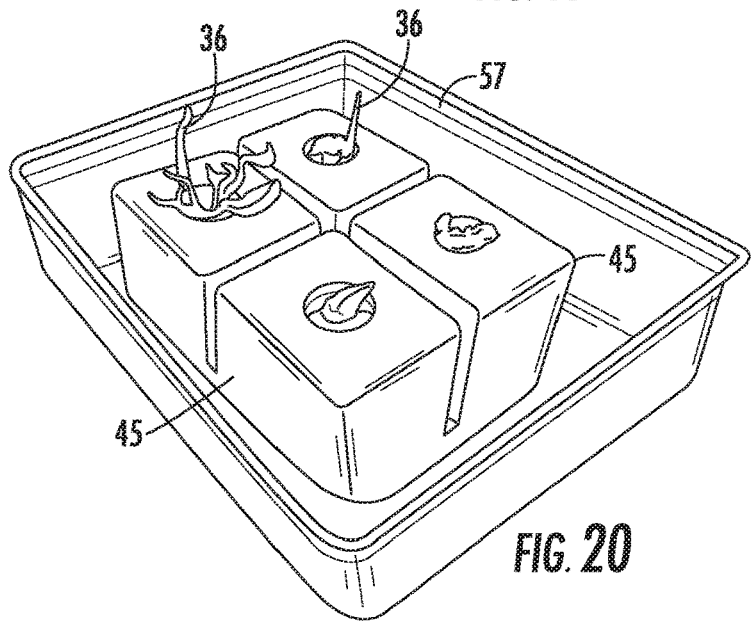
FIG. 20 illustrates plant material following transplantation to a receiver.
Figure 21:
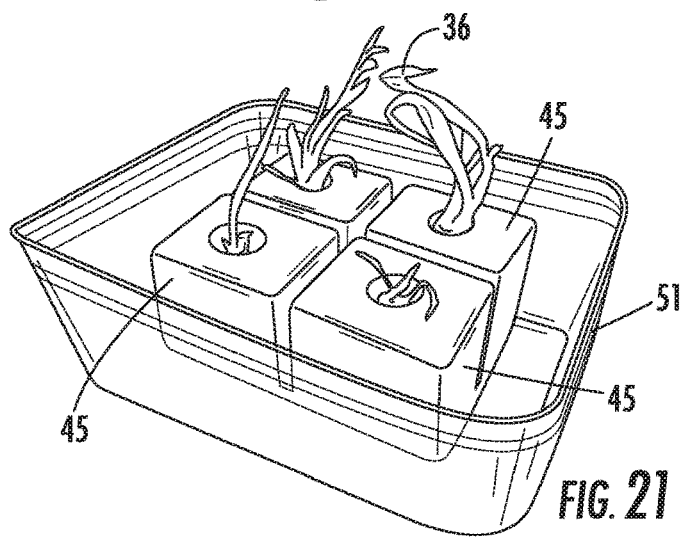
FIG. 21 illustrates plant material following transplantation to and further cultivation on a receiver.

The developing plants can be held in a receiver 40 until transfer to another receiver or transfer to soil in a greenhouse or in the environment. A single container can be used to hold the receiver throughout this stage or the container can be changed, depending on the desired growth circumstances of the plants. For instance, FIG. 20 and FIG. 21 illustrate four receiving areas 45 that have been removed from the remainder of a larger receiver and transferred to a more traditional container 57 for further development. The transfer of one or more receiving areas from a first container to a second container can be carried out due to a desired change in growth media and/or atmospheric environment, due to the increasing size of the plantlet, or for any other desired purpose.

Figure 22:
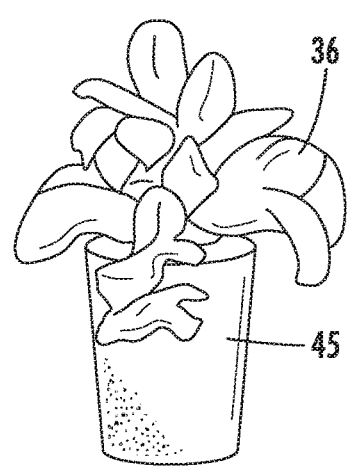
FIG. 22 illustrates a single receiving area following separation from the remainder of a receiver.

Once developed into a small plant capable of surviving in soil, the plant can be transplanted. For instance, the container 57 can be opened (if necessary), and an individual receiving area 45 (FIG. 22) can be separated from other receiving areas 45 to which it has been attached (for instance by use of a hands-free tool, in some embodiments). In those embodiments in which the receiving area is formed of a degradable porous material, such as a degradable foam, the receiver 45, which carries a young plant 36, may be voided of organic compounds by rinsing, and can then be transplanted in its entirety, with no need for separation of the young plant from the tissue support matrix, which can increase likelihood of the plants long-term survival.

In one embodiment, the initial growth and development stages of the plant tissue while held in the plant tissue cassette and receiver can be carried out in a laboratory setting, for instance under a predetermined growth schedule and with controlled lighting sources. The systems can optionally be utilized for growth and development of the plant material within a greenhouse. For example, initial growth and development in the plant tissue cassette can be carried out in a laboratory setting, and the system can be moved to a greenhouse after the plant material has been transferred to a receiver and at a time that the developing plant material is strong enough. Further development can then be carried out in the greenhouse.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A method for plant propagation comprising:
   locating plant material that is heterotrophic on a sterilized support area of a plant tissue cassette;
   cultivating the plant material in conjunction with a first liquid growth media for a first period of time during which the plant material is supported on the support area and the plant tissue cassette is retained within a first sterilized container, the first liquid growth material comprising an extraneous source of carbon;
   separating the support area and the plant material supported thereon from the remainder of the plant tissue cassette following the first period of time, wherein the plant material has developed autotrophic capability at the time of the separation;
   locating the separated support area and the plant material supported thereon on a sterilized receiving area of a receiver;
   cultivating the plant material in conjunction with a second liquid growth media for a second period of time during which the plant material is supported on the support area and the receiving area and during which the receiver is retained within a second sterilized container;
   separating the receiving area and the plant material and the support area supported thereon from the remainder of the receiver following the second period of time; and
   transplanting the plant material into soil.

2. The method of claim 1, wherein the plant material that is heterotrophic comprises dedifferentiated callus or undifferentiated meristematic cells.

3. The method of claim 1, wherein the plant material that is heterotrophic comprises transformed tissue, a somatic embryo, or a zygotic embryo.

4. The method of claim 1, wherein the first liquid growth media comprises sucrose.

5. The method of claim 1, wherein the plant material develops initial roots and shoots during the second period of time.

6. The method of claim 5, wherein the receiving area comprises a degradable foam, the developing roots growing into the receiving area during the second period of time.

7. The method of claim 1, wherein the plant material is transplanted into the soil in conjunction with the support area and the receiving area.

* * * * *